United States Patent [19]

Bayley

[11] 4,131,443
[45] Dec. 26, 1978

[54] FUSED SILICA NUCLEAR MAGNETIC RESONANCE AND FILTER CELLS WITH STABILIZED VAPOR DENSITIES

[75] Inventor: Donald S. Bayley, Bedford, N.Y.

[73] Assignee: The Singer Company, Little Falls, N.J.

[21] Appl. No.: 765,136

[22] Filed: Feb. 2, 1977

[51] Int. Cl.² .................. C03B 5/16; G01N 27/00; G02B 5/24
[52] U.S. Cl. ........................... 65/17; 65/32; 65/34; 350/312; 316/20; 324/0.5 AH
[58] Field of Search ............. 324/0.5 AH; 65/32, 34, 65/17; 350/312; 316/20; 29/592

[56] References Cited

U.S. PATENT DOCUMENTS

| | | | |
|---|---|---|---|
| 1,464,698 | 8/1923 | Delany | 65/34 X |
| 3,178,864 | 4/1965 | Anderson et al. | 65/32 X |
| 3,721,541 | 3/1973 | Simpson et al. | 65/34 X |
| 3,817,733 | 6/1974 | Thuler | 65/278 X |
| 4,045,201 | 8/1977 | Caffarella et al. | 65/271 X |

OTHER PUBLICATIONS

Introduction to Atomic Spectra by Harvey Elliott White, Ph.D., McGraw-Hill Book Co., N.Y. 1934, pp. 77-85.

Primary Examiner—S. Leon Bashore
Assistant Examiner—F. W. Miga
Attorney, Agent, or Firm—Thomas W. Kennedy

[57] ABSTRACT

After being baked out to remove absorbed gases, fursed silica cell blanks are cooled from a temperature of around 900° C. to a temperature of around 800° C. over a period of at least two hours. After the blanks are cooled to room temperature, an unsaturated vapor of atoms having an $S_o$ ground state is driven into the cell blanks from a reservoir. The cell blanks and the vapor contained therein are subjected to optical resonance radiation for around four hours at room temperature while the cell blanks are connected to the reservoir. A prescribed vapor density is established in the cell blanks before they are sealed off from the reservoir.

8 Claims, 1 Drawing Figure

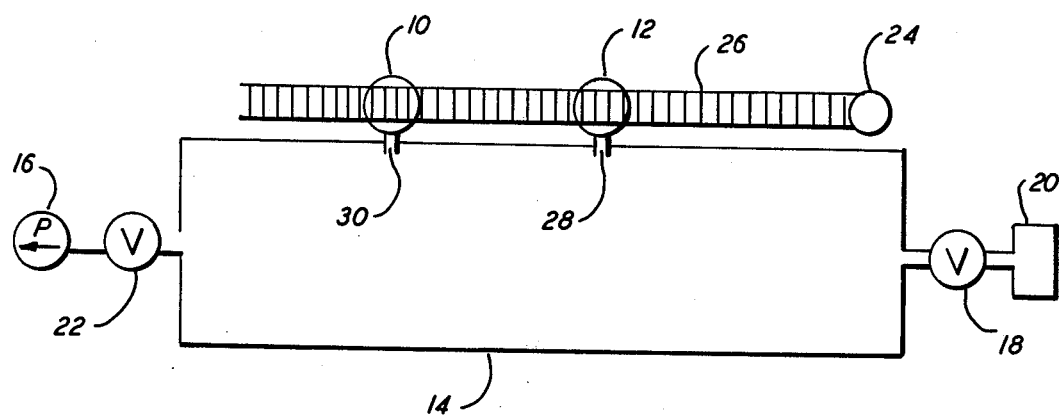

FUSED SILICA NUCLEAR MAGNETIC RESONANCE AND FILTER CELLS WITH STABILIZED VAPOR DENSITIES

BACKGROUND OF THE INVENTION

Field of the Invention

The invention herein described was made in the course of or under a contract, or subcontract thereunder, with the Department of the Air Force.

This invention relates generally to fused silica cells containing a vapor of atoms having an $S_0$ ground state and particularly to such cells with stabilized vapor density.

Description of the Prior Art

Cells are used in current nuclear magnetic resonance apparatus to contain the vapor in which the resonance is to be established or which is to be used as an optical filter. The vapor can be composed of atoms having an $S_0$ ground state and the cell can be composed of fused silica.

As is known in the art and is described more fully in the text "Introduction to Atomic Spectra" by Harvey Elliott White, Ph.D., an $S_0$ ground state means that the electrons in the outer shell are symmetrical and do not contribute to the moments of the cell. The S indicates that there is no angular momentum and the "$_0$" that there is no spin angular momentum. In other words, the electrons are grouped in pairs and the spins of the electrons cancel. The elements which satisfy these conditions are all the elements in the second column of the periodic table and inert gasses.

Procedures are known for the manufacture of fused silica cells containing unsaturated vapor. The major disadvantage of cells manufactured according to these procedures is that the vapor density within the cell changes as the atoms are exposed to optical resonance radiation. This density change affects the transmission of radiation through the cell and the strength of the nuclear magnetic resonance (NMR) signal.

SUMMARY OF THE INVENTION

It is therefore an object of the invention to provide a fused silica cell containing the unsaturated vapor of atoms having an $S_0$ ground state which overcomes the aforementioned problem of changing vapor density. It is also an object of the invention to provide a fused silica cell whose transmission and NMR signal strength do not vary when the cell is exposed to optical resonance radiation.

These and other objects of the invention are achieved in a fused silica cell containing a vapor of atoms having an $S_0$ ground state. Fused silica cell blanks are baked out until the residual gas pressure in the cell blanks is reduced to around $10^{-7}$ torr. The cell blanks are cooled from a temperature of around 900° C. to a temperature of around 800° C. over a period of at least two hours. The cell blanks are then cooled to room temperature. The vapor is driven from a reservoir into the cell blanks. While connected to the reservoir, the cell blanks and the vapor contained therein are exposed to optical resonance radiation for around four hours at room temperature. A prescribed vapor density is established within the cell blanks and the cell blanks are then sealed off from the reservoir.

These and other features of the invention will be described in greater detail in the following detailed description.

BRIEF DESCRIPTION OF THE DRAWINGS

The FIGURE is a schematic illustration of an apparatus for manufacturing a fused silica cell in accordance with the invention.

DETAILED DESCRIPTION

Referring now to the drawing, there is shown, in schematic form, fused silica cell blanks 10 and 12 attached to manifold 14. Vacuum pump 16 evacuates manifold 14 and cell blanks 10 and 12 to a pressure of about $10^{-7}$ torr while the cell blanks are held at a temperature of at least 950° C., but less than the melting point of fused silica, by a heater, not shown, for around sixteen hours. Other known bake-out procedures can be used, of course.

Evacuated reservoir 20 contains that material composed of atoms having an $S_0$ ground state that is desired in the finished cells. Various isotopes of mercury are typically used, although cadmium and zinc are also useable materials. During this time valve 18 is closed to prevent the escape of the contents of reservoir 20 into manifold 14, but valve 22 of course is open. After this sixteen-hour period, cell blanks 10 and 12 are allowed to cool. The blanks are cooled slowly, however, from a temperature of around 900° C. to a temperature of around 800° C. Typically, the cell blanks are cooled from a temperature of 900° C. to a temperature of 800° C. over a period of at least two hours. The cell blanks are then cooled to room temperature. Once the blanks cool, valve 18 is opened to permit vapor of the desired material from reservoir 20 to enter manifold 14 and valve 22 is closed. The vapor is driven into cell blanks 10 and 12 by holding the cell blanks at a lower temperature than reservoir 20 and manifold 14.

Cell blanks 10 and 12 and the vapor contained therein are then exposed to optical resonance radiation 26 for around four hours at room temperature. Optical resonance radiation 26 is emitted from light source 24. If the vapor is composed of mercury, light source 24 could be a Hg lamp. Reservoir 20 is then held at room temperature and cell blanks 10 and 12 are held at a slightly higher temperature while the cell blanks are sealed off at their openings 30 and 28 forming cells which enclose a prescribed amount of the desired vapor.

It has been found that mercury vapor density inside cells formed as described above remains stable even when the sealed off cells are subsequently exposed to optical resonance radiation.

Especially good results have been achieved where reservoir 20 was at a temperature of 25° C. when the cell blank was sealed off. This cell maintained a large vapor density even at low cell temperatures. The transmission through this cell decreased from around 56% at 13° C. to around 23% at 42° C., the apparent dry point, where the vapor first became unsaturated.

Optical resonance radiation had no effect on the transmission at any temperature. After a heat treatment consisting of maintaining the cell at a temperature of about 1000° C. for an hour, strong NMR signals were obtained from the cell at all temperatures between 90° C. and 400° C. Such heat treatments did not appreciably change the transmission characteristics of this cell.

Fused silica cells prepared in accordance with this invention are especially useful as filter cells in nuclear magnetic resonance apparatus. These cells are made with unsaturated vapor to increase the stability of the filter characteristics against temperature. Fused silica cells made by the prior methods are not satisfactory as filter cells, however, because optical resonance radiation changes the vapor density and the filter characteristics of the cell. Fused silica cells made according to this invention, however, have a stable mercury vapor density and, when used as a filter, stable filter characteristics.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawing are, accordingly, to be regarded in an illustrative rather than in a restrictive sense.

What is claimed is:

1. A method for making fused silica cells containing an unsaturated vapor of atoms having an $S_o$ ground state, such that the cells will have a stable vapor density, comprising:
   (a) removing absorbed gases from fused silica cell blanks by baking out the cell blanks until the pressure of the absorbed gases in the cell blanks is reduced to around $10^{-7}$ torr;
   (b) cooling the cell blanks from a temperature of around 900° C. to a temperature of around 800° C. over a period of at least two hours;
   (c) cooling the cell blanks to room temperature;
   (d) driving the vapor from a reservoir into the cell blanks;
   (e) subjecting the cell blanks and the vapor contained therein to optical resonance radiation for around four hours at room temperature while the cell blanks are connected to the reservoir;
   (f) establishing a prescribed vapor density within the cell blanks; and
   (g) sealing off the cell blanks when the prescribed vapor density has been established.

2. The method as recited in claim 1 wherein the prescribed vapor density is established by holding the reservoir at a predetermined temperature and the cell blanks at a slightly higher temperature.

3. The method as recited in claim 2 wherein the reservoir is held at a temperature corresponding to a saturated vapor pressure of the desired vapor of around 0.0018 torr.

4. The method as recited in claim 1 wherein the prescribed vapor density within the cell blank corresponds to a saturated vapor pressure of the desired vapor of around 0.0018 torr.

5. The method as recited in claim 1 wherein the vapor driven from the reservoir is cadmium.

6. The method as recited in claim 1 wherein the vapor driven from the reservoir is zinc.

7. The method as recited in claim 1 wherein the vapor driven from the reservoir is mercury.

8. A method for making fused silica cells containing mercury for use in nuclear magnetic resonance apparatus, such that the cells will have a stable mercury vapor density, comprising:
   (a) removing absorbed gases from fused silica cell blanks by baking out the cell blanks until the pressure of the absorbed gases in the cell blanks is reduced to around $10^{-7}$ torr;
   (b) cooling the cell blanks slowly from a temperature of around 900° C. to a temperature of around 800° C. over a period of at least two hours;
   (c) cooling the cell blanks to room temperature;
   (d) driving mercury from a mercury reservoir into the cell blanks;
   (e) exposing the cell blanks and the mercury vapor contained therein to optical resonance radiation for around four hours at room temperature while the cell blanks are connected to the mercury reservoir; and
   (f) sealing off the cell blanks while holding the reservoir at a temperature of around 25° C. and the cell blanks at a slightly higher temperature.

* * * * *